US008744211B2

(12) United States Patent
Owen (10) Patent No.: US 8,744,211 B2
(45) Date of Patent: Jun. 3, 2014

(54) MULTI-MODALITY IMAGE ACQUISITION

(75) Inventor: Robert H. Owen, Stenløse (DK)

(73) Assignee: Analogic Corporation, Peabody, MA (US)

( * ) Notice: Subject to any disclaimer, the term of this patent is extended or adjusted under 35 U.S.C. 154(b) by 79 days.

(21) Appl. No.: 13/222,269

(22) Filed: Aug. 31, 2011

(65) Prior Publication Data

US 2013/0053679 A1 Feb. 28, 2013

(51) Int. Cl.
*G06K 9/64* (2006.01)
*A61B 5/055* (2006.01)
*A61B 8/00* (2006.01)
*G06T 7/00* (2006.01)
*A61B 8/08* (2006.01)
*A61B 6/00* (2006.01)
*A61B 6/03* (2006.01)

(52) U.S. Cl.
CPC .............. *G06T 7/0026* (2013.01); *A61B 8/483* (2013.01); *A61B 8/5246* (2013.01); *A61B 6/5247* (2013.01); *A61B 8/4245* (2013.01); *A61B 8/4254* (2013.01); *A61B 8/5261* (2013.01); *G06T 7/0028* (2013.01); *G06T 7/0042* (2013.01); *A61B 6/032* (2013.01); *A61B 6/037* (2013.01); *A61B 5/055* (2013.01)
USPC ............................ 382/278; 600/411; 600/443

(58) Field of Classification Search
CPC ...... A61B 6/032; A61B 6/037; A61B 6/5247; A61B 5/055; A61B 8/483; A61B 8/5246; A61B 8/4245; A61B 8/4254; A61B 8/5261; G06T 7/0026; G06T 7/0028; G06T 7/0042
USPC .......... 600/411, 424, 437, 443; 382/128, 131, 382/276, 278, 284
See application file for complete search history.

(56) References Cited

U.S. PATENT DOCUMENTS

| 7,639,895 | B2 * | 12/2009 | Sakas et al. | 382/284 |
|---|---|---|---|---|
| 7,669,129 | B2 * | 2/2010 | Mathur | 715/723 |
| 8,233,681 | B2 * | 7/2012 | Aylward et al. | 382/128 |
| 2005/0182319 | A1 * | 8/2005 | Glossop | 600/424 |
| 2009/0053208 | A1 * | 2/2009 | Nayak | 424/130.1 |

* cited by examiner

*Primary Examiner* — Michael Rozanski
(74) *Attorney, Agent, or Firm* — Cooper Legal Group LLC (57) ABSTRACT

One or more techniques and/or systems are described for automatically generating a transformation matrix for correlating images from an ultrasound modality with images from another modality (or with ultrasound images acquired at a different point in time). Ultrasound volumetric data and volumetric data yielded from another image modality are examined to identify and/or extract features. The transformation matrix is automatically generated, or populated, based at least in part upon common features that are identified in both the ultrasound volumetric data and the volumetric data yielded from the other image modality. The transformation matrix can then be used to correlate images from the different modalities (e.g., to display a CT image of an object next to an ultrasound image of the object, where the images are substantially similar to one another even though they were acquired using different modalities).

20 Claims, 6 Drawing Sheets

MULTI-MODALITY IMAGE ACQUISITION

BACKGROUND

The present application relates to image fusion (e.g., also referred to as image registration). It finds particular application in medical examinations and/or treatments where viewing an object using two or more image modalities may be useful. For example, as provided herein, images yielded from examining an object using a first image modality may be correlated with images yielded from examining the object using an ultrasound modality based upon a transformation matrix that is automatically generated. In this way, as medical personnel alter the view of an object as represented in ultrasound images, a view of the object as represented in images yielded from the first image modality may be automatically altered in a corresponding manner such that both images that are displayed on a screen represent a substantially similar viewpoint of the object, for example. It will be appreciated that while particular reference is made herein to medical applications, the features described herein may also be applied to other applications, such as security and/or industrials applications.

Today, a plurality of image modalities exists for imaging an object under examination. The particular image modality that is used may depend upon numerous factors, including, but not limited to, which aspect(s) of the object a medical professional desires to examine. For example, medical sonography (e.g., one form of ultrasound) is frequently used to visualize muscles, tendons, and/or organs of a patient, whereas conventional x-ray systems are typically used to visualize the skeletal system of a patient. Accordingly, it may be that, in some applications, such as in numerous medical applications, an aspect of an object to be examined and/or treated may be imaged using more than one image modality to leverage off of the respective benefits of different modalities. For example, computed tomography (CT) systems have become an important tool to supplement x-rays and medical sonography because CT systems can generally produce higher contrast images than x-ray systems and/or ultrasound systems (e.g., such that differences between tissues that differ in density by less than 1% can be distinguished). Magnetic resonance imaging (MRI) systems are another type of image modality that has been used to supplement x-rays and medical sonography because of the contrast MRI systems provide in images.

To improve upon the usefulness (e.g., diagnostic advantages and/or treatment planning capabilities) of the data collected from two or more image modalities, a process known as image fusion may be performed. Generally speaking, image fusion is the process of combining or correlating relevant data from two or more image modalities. Traditionally, the data from the two image modalities was literally combined during image fusion, such that a technician was typically viewing a monitor that essentially comprised an image acquired from a first image modality overlaid on top of an image acquired from a second image modality. However, the more modern approach is to correlate but not combine the data from the two or more image modalities. Thus, an image representing a first perspective of an object acquired using a first image modality may be situated side-by-side on a monitor(s) with an image representing a substantially similar perspective of the object acquired using a second image modality. When a technician alters the perspective of the object as represented by an image acquired using the second image modality (e.g., which may be imaging the object in real-time), the perspective of the object as represented by an image acquired using the first image modality (e.g., which may have imaged the object weeks earlier) may be reoriented to reflect the alteration made to the orientation of the object represented in the image(s) acquired using the second image modality. In this way, a user is typically viewing side-by-side images, acquired from different image modalities, that depict an object from a substantially similar viewpoint.

While image fusion has proven successful for combining data collected using two or more image modalities, the ability to fuse or correlate data acquired from an ultrasound system with data acquired from another image modality (e.g., acquired at a same or different time) has proven to be elusive. For example, when a technician wishes to fuse ultrasound data with data acquired from another image modality and/or with ultrasound data acquired at a different time (e.g., such as weeks earlier), the technician generally manually aligns the ultrasound images with the images yielded from another image modality to generate a transformation matrix that is based upon the manual alignment. Such a manual alignment is generally time intensive, introduces human error, and can be performed merely by those with expertise in interpreting both ultrasound images and the images yielded from the other image modality(ies) with which the technician desires to fuse or correlate the ultrasound image(s).

SUMMARY

Aspects of the present application address the above matters, and others. According to one aspect a multi-modality image registration method is provided. The method comprises automatically generating a transformation matrix to be used for correlating an image from an examination of an object using a first image modality with an image yielded from an ultrasound examination of the object.

According to another aspect a system for multi-modality image correlation is provided. The system comprises a feature correlation component configured to automatically generate a transformation matrix to be used for correlating an image yielded from an examination of an object using a first image modality with an ultrasound image yielded from an ultrasound examination of the object.

According to yet another aspect, a computer-readable storage medium comprising computer executable instructions that when executed via a processor perform a method is provided. The method comprises correlating a first image yielded from an examination of an object using a first image modality and a second image yielded from an examination of the object using an ultrasound modality based at least in part upon an automatically generated transformation matrix.

Those of ordinary skill in the art will appreciate still other aspects of the present application upon reading and understanding the appended description.

FIGURES

The application is illustrated by way of example and not limitation in the figures of the accompanying drawings, in which like references generally indicate similar elements and in which.

DESCRIPTION

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

One or more systems and/or techniques are provided for automatically generating a transformation matrix that can be used to correlate an ultrasound image of an object yielded from an ultrasound modality with a second image of the object yielded from another image modality and/or with a second image of the object yielded from the ultrasound modality (e.g., which may have been captured weeks earlier than ultrasound image). Other image modalities that can produce images which may be correlated with the ultrasound image include, but are not limited to MRI, CT, positron emission tomography (PET), single photon emission computed tomography (SPECT), and/or other image modalities that are configured to (e.g., able to) construct a three-dimensional (3D) and/or four-dimensional (4D) representation of an object or aspect of an object under examination.

As an example of where one or more of the systems and/or techniques described herein may be useful, an object may be imaged by a first image modality, such as a CT image modality, prior to a surgery to identify cancerous tissue of a patient and develop a 3D CT representation of the tissue from which a treatment plan may be developed. Subsequently, immediately before the surgery and/or during surgery, the object may be reimaged by an ultrasound modality to determine how to proceed with the surgery given the orientation of the patient/tumor and/or to monitor the insertion of surgical instruments into the patient during the surgery. Based upon the 3D CT representation and ultrasound volumetric data constructed from a plurality of ultrasound images (e.g., respectively depicting a parallel plane of the object), a transformation matrix may be automatically generated. The transformation matrix may subsequently be used to correlate a CT image derived from CT volumetric data with a given ultrasound image and/or vice-versa.

It will be appreciated that while examples are provided herein of medical applications, the instant disclosure is not intended to be limited as such. For example, the features described herein may be applicable in security and/or industrial applications where an ultrasound modality and one or more other image modalities (e.g., capable of yielding volumetric data) may be used to image an object. Moreover, while specific reference is made herein to several different types of volumetric image modalities, it will be appreciated that to the extent practicable, the instant application, including the scope of the claims, is not intended to be limited as such. That is, other types of image modalities that are configured to and/or capable of yielding three-dimensional, four-dimensional, etc. data of an object under examination are contemplated for use herein.

Further, it will appreciated that while specific configurations are illustrated in the example figures and described herein, the instant application, including the scope of the claims, is not intended to be limited as such to the extent practicable. That is, the figures and the details provided herein, such as how two or more components are coupled together, are merely provided as examples to provide clarity and understanding. For example, two or more of the components described herein (e.g., such as the detector array 106 and the data acquisition component 122 of FIG. 1) may be part of a single component and/or functions that are described as being performed by a single component herein may be separated into two or more different components. Further, the systems and/or techniques may comprise additional features and/or fewer features than those described herein. Stated differently, the figures and accompanying description is not intended to be interpreted in a limiting manner, such as necessarily specifying the location, inclusion, and/or relative arrangement of the components described herein, for example.

Figure 1:
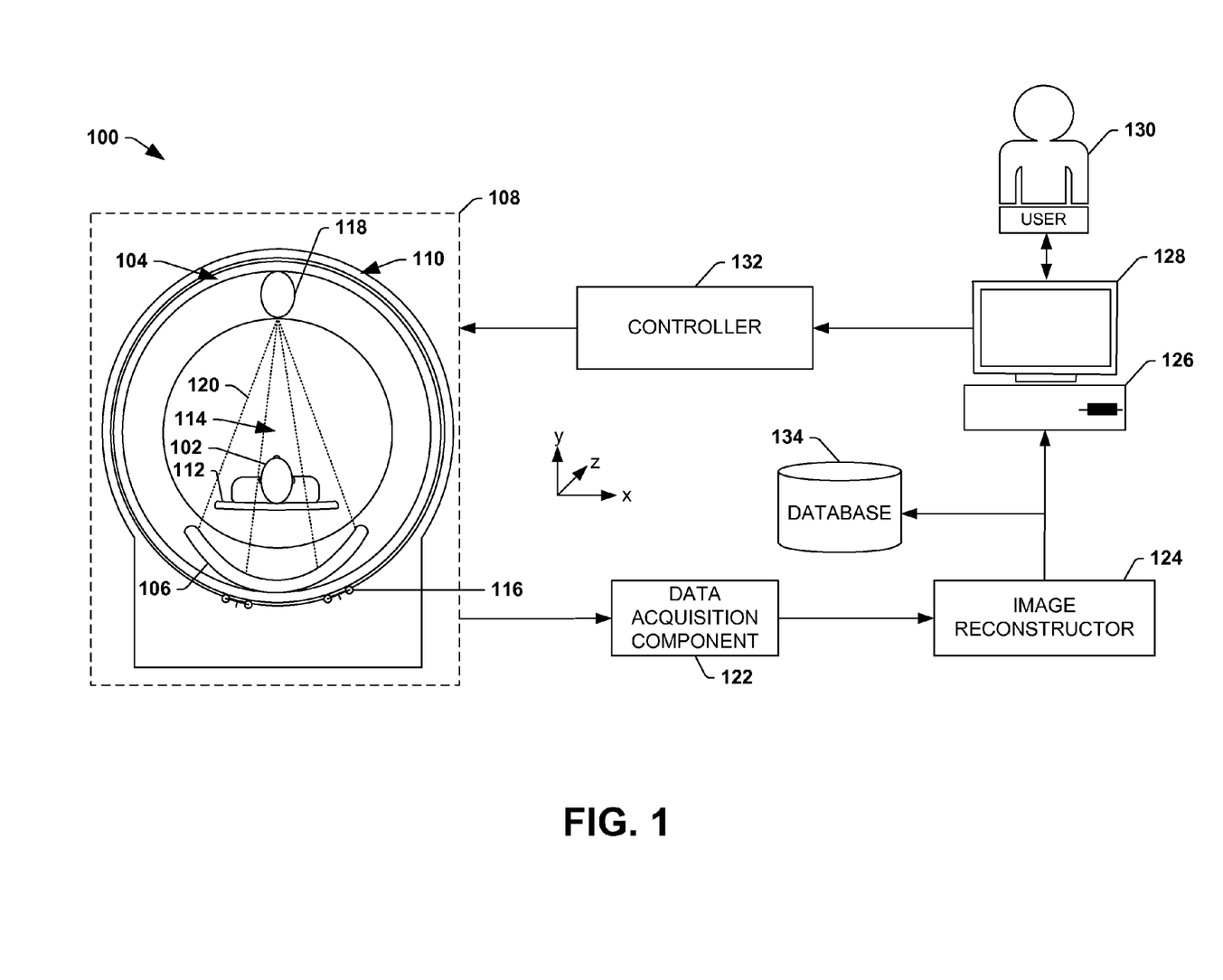
FIG. 1 is an example environment of a first image modality configured to examine an object and produce volumetric data therefrom.

FIG. 1 is an illustration of an example environment 100 of an example image modality that may be configured to generate volumetric data (e.g., and resulting images) representative of an object or an aspect thereof under examination. More particularly, the example environment 100 illustrates an example CT image modality that can be configured to acquire volumetric information regarding an object 102, such as a patient, under examination and generate two-dimensional and/or three-dimensional images therefrom. It will be appreciated that a CT image modality is merely one of the numerous image modalities that are contemplated herein and is described herein merely to provide one example image modality that may yield volumetric data representative of an object 102 under examination from which one or more images may be derived. Other image modalities, such as, but not limited to, those provided above, are also contemplated herein.

In the example environment 100, an examination unit 108 of the CT image modality is configured to examine one or more objects 102. The examination unit 108 can comprise a rotating gantry 104 and a (stationary) support structure 110 (e.g., which may at least partially encase and/or surround as least a portion of the rotating gantry 104 (e.g., as illustrated herein with an outer, stationary ring, surrounding an outside edge of an inner, rotating ring)). During an examination of the object(s) 102, the object(s) 102 can be placed on a support article 112, such as a bed, for example, that is selectively positioned in an examination region 114 (e.g., a hollow bore in the rotating gantry 104), and the rotating gantry 104 can be rotated and/or supported about the object(s) 102 by a rotator 116, such as a motor, drive shaft, chain, roller truck, etc.

The rotating gantry 104 may surround a portion of the examination region 114 and may comprise one or more radiation sources 118 (e.g., an ionizing x-ray source) and a detector array 106 comprised of a plurality of pixels (e.g., also referred to as detectors) that is mounted on a substantially diametrically opposite side of the rotating gantry 104 relative to the radiation source(s) 118.

The detector array 106 can comprise a linear or two-dimensional array of pixels disposed as a single row or multiple rows in the shape of a circular, cylindrical, or spherical arc, for example, typically having a center of curvature at a focal spot of the radiation source 118 (e.g., the point within the radiation source 118 from which radiation 120 emanates), for example. During an examination of the object(s) 102, the radiation source(s) 118 emits fan, cone, wedge, and/or other shaped radiation 120 configurations from the focal spot and into the examination region 114. It will be appreciated that such radiation 120 may be emitted substantially continuously and/or may be emitted intermittently (e.g., a short pulse of radiation is emitted followed by a resting period during which the radiation source 118 is not activated).

As the emitted radiation 120 traverses the object(s) 102, the radiation 120 may be attenuated differently by different aspects of the object(s) 102. Because different aspects attenuate different percentages of the radiation 120, an image(s) may be generated based upon the attenuation, or variations in the number of radiation photons that are detected by the detector array 106. For example, more dense aspects of the object(s) 102, such as a bone, may attenuate more of the radiation 120 (e.g., causing fewer photons to strike the detector array 106) than less dense aspects, such as skin or clothing.

As the rotating gantry 104 rotates, the detector array 106 is configured to directly convert (e.g., using amorphous selenium and/or other direct conversion materials) and/or indirectly convert (e.g., using photodetectors and/or other indirect conversion materials) detected radiation into analog signals that can be transmitted from the detector array 106 to a data acquisition component 122 configured to periodically sample the analog signal generated by respective pixels (e.g., respectively comprising one or more channels) and generate a digital output signal representative of one or more characteristics (e.g., density, z-effective, etc.) of a portion of the object 102 being examined during that measuring interval.

The collection of digital output signals generated by the data acquisition component 122 for a measuring interval and yielded from the analog signals respectively output by the pixels of the detector array 106 may be referred to as a "projection" or a "view". Moreover, the angular orientation of the rotating gantry 104 (e.g., and the corresponding angular orientations of the radiation source(s) 118 and the detector array 106) during generation of a projection may be referred to as the "projection angle."

As the rotating gantry 104 rotates around the object 102 under examination, the data acquisition component 122 generates a plurality of projections at a corresponding plurality of projection angles. It will be appreciated that the term "measured projection data" and/or the like is used herein to refer to this plurality of projections that are generated by the data acquisition component 122 and is indicative of the amount of radiation that the detector array 106 detected or measured.

The example environment 100 further comprises an image reconstructor 124 configured to receive the measured projection data output by the data acquisition component 122. The image reconstructor 124 is also configured to use analytical, iterative, and/or other image reconstruction algorithms and/or techniques to generate image data from the measured projection data (e.g., 2D filtered-backprojection, iterative backprojection, etc.). Thus, the image reconstructor 124 may be configured to convert the measured projection data into volumetric data in image space. In this way, the data is converted from projection space to image space, a domain that may be more understandable by a user 130 viewing the image(s), for example.

The example environment 100 also includes a terminal 126, or workstation (e.g., a computer), configured to receive image(s) from the image reconstructor 124, which can be displayed on a monitor 128 to the user 130 (e.g., security personnel, medical personnel, etc.). In a CT image modality, a displayed image(s) is typically a representation of one or more characteristics (e.g., density, z-effective, etc.) of a two-dimensional "slice" of the object (e.g., taken from the volumetric data) during the rotation of the rotating gantry 104 through the various projection angles. In this way, a user 130 can inspect the image(s) to identify areas of interest within the object(s) 102. The terminal 126 can also be configured to receive user input which can direct operations of the object examination apparatus 108 (e.g., a speed of rotation, an energy level of the radiation, etc.).

In the example environment 100, a controller 132 is operably coupled to the terminal 126. In one example, the controller 132 is configured to receive user input from the terminal 126 and generate instructions for the examination unit 108 indicative of operations to be performed.

As illustrated, the example environment 100 of the CT image modality may further comprise a database 134 (e.g., a computer readable storage device such as a hard drive, flash drive, solid state device, etc.) configured to store at least some of the data that is produced by the CT image modality so that data can be selectively recalled at a later time. For example, the volumetric data yielded from the image reconstructor 124 may be stored in the database 134 and at least some of the volumetric data may be retrieved at a later time (e.g., such as when image fusion is performed). In another embodiment, the measured projection data yielded from the data acquisition component 122 may be stored in the database 134, and prior to image fusion, at least some of the measured projection data may be retrieved from the database 134 and converted into volumetric data by the image reconstructor 124, for example. Thus, the database 134 is configured to store at least some of the data yielded from the first image modality (e.g., CT image modality), so that it can be further processed at a later time (e.g., after the patient examination using the first image modality has been completed).

It will be appreciated that while reference is made herein to respective components being part of the CT image modality, one or more of the aforementioned components may not be comprised in the CT image modality illustrated in the example environment 100, but may instead by operably coupled to the CT image modality. For example, the database 134 may be operably coupled to the CT image modality via a network, and the database 134 may be a resource shared with other components/systems (e.g., and can be configured to store data from two or more image modalities).

Figure 2:
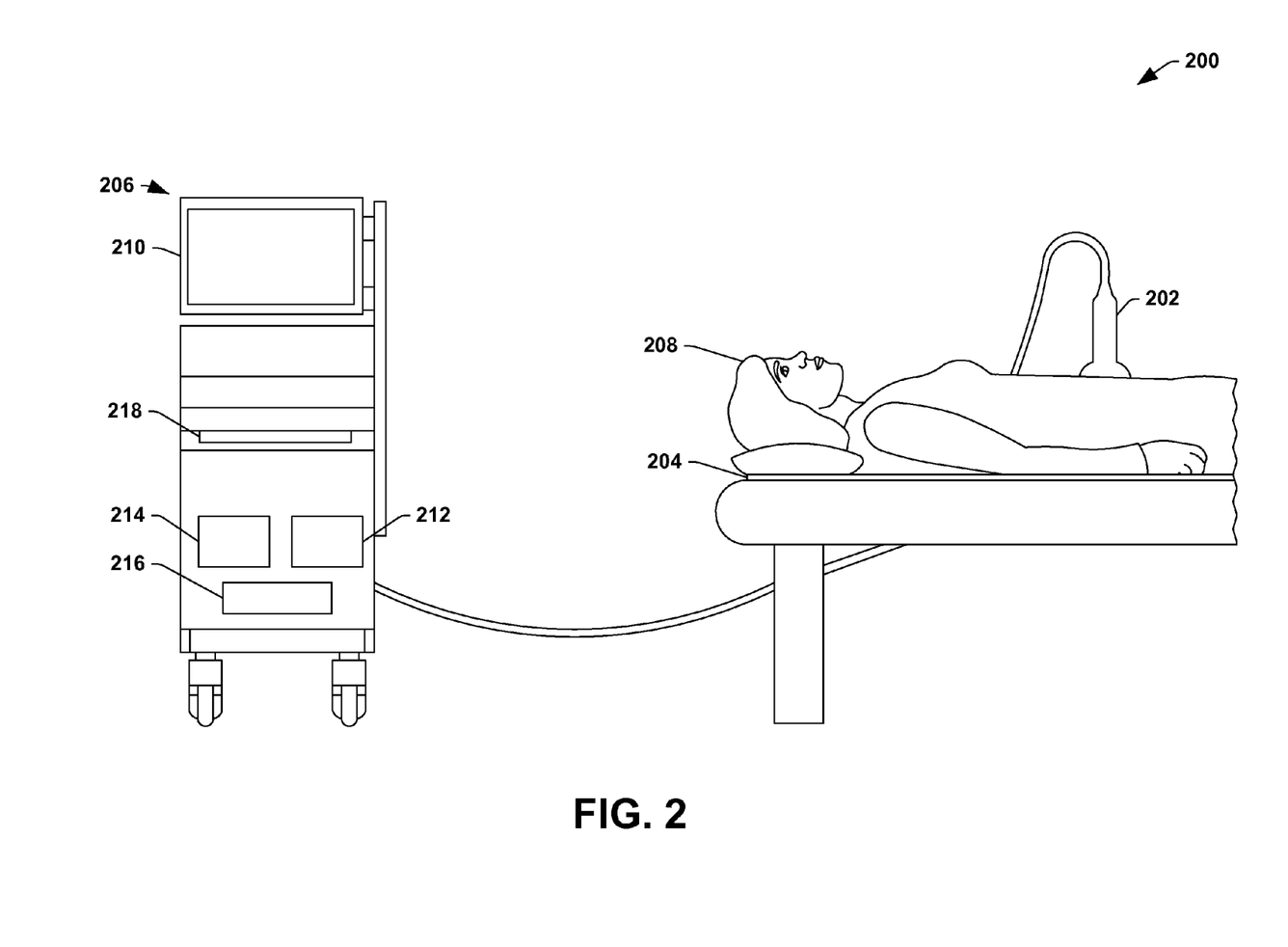
FIG. 2 is an example environment of an ultrasound modality configured to examine an object and produce volumetric data therefrom.

FIG. 2 illustrates an example environment 200 of another image modality. More specifically, FIG. 2 illustrates an example ultrasound modality that is configured to yield volumetric ultrasound data of an object or an aspect thereof under examination. It will be appreciated that the example ultrasound modality is merely intended to illustrate one example of an ultrasound modality and other ultrasound modalities are also contemplated herein.

As illustrated, the ultrasound modality comprises one or more ultrasounds probes 202, a volumetric data generator (e.g., comprising a tracking component 204), and a processing unit 206. The ultrasound probe(s) 202 are configured to transmit ultrasound signals (e.g., sound waves generally in the range of 2 MHz to 10 MHz) towards an object 208 (e.g., 102 in FIG. 1) or aspect thereof under examination and/or receive echo signals resulting from the ultrasound signals. Stated differently, ultrasound signals are emitted via the ultrasound probe(s) 202 into the object 208 and responses to those signals (e.g., signals reflected back toward the ultrasound probe 202 due at least in part to an interaction with the object) are measured. Based upon the echoes (e.g., and how long it took for the echoes to be received after the ultrasound signals were emitted) images of the aspect of the object 208 under examination can be produced.

It will be appreciated that there are numerous types of ultrasound probes, respective probes configured differently. For example, some ultrasound probes may be configured to merely emit ultrasound signals and may be used in conjunction with other ultrasound probes that are configured to merely detect or listen for echoes. Other ultrasound probes may be configured to both emit ultrasound signals and listen for echoes. For purposes of the instant disclosure, the types of ultrasound probes that can be used are not intended to be limited to one or more particular types. That is, to the extent practicable, virtually any type of ultrasound probe may be used to examine the object 208 or an aspect thereof and the selection of a particular type of ultrasound probe to use may depend at least in part upon the aspect of the object 208 to be examined, a condition of the object 208, and/or an orientation of the object 208, for example.

The example ultrasound modality further comprises a tracking component 204 (e.g., a tracking mat), that is configured to track a position of the ultrasound probe(s) 202 relative to the object 208 under examination and/or relative to the tracking component 204 and to generate position information based upon the tracking. For example, in one embodiment, the tracking component 204 may be part of a passive or active magnetic tracking system. For example, in a passive magnetic tracking system, the tracking component 204 may comprise a magnetic mat that is positioned substantially diametrically opposite the ultrasound probe(s) 202 (e.g., in the illustrated Fig., the object 208 is lying on the mat), and the ultrasound probe 202 may comprise a piece of metal that can be detected by the tracking component 204. As the probe moves about the object 208, the magnetism at various parts of the mat may change, allowing the position of the ultrasound probe(s) 202 to be tracked. Alternatively, in an active magnetic tracking system, the tracking component 204 may comprise a magnetic field generator, for example, and the ultrasound probe 202 may comprise a field tracking component configured to track a position of the ultrasound probe 202 relative to a magnetic field generated by the magnetic field generator, for example.

While a magnetic tracking system provides one means of tracking an ultrasound probe(s) 202, it will be appreciated that there are numerous other ways that an ultrasound probe(s) 202 can be tracked. For example, in another embodiment, the tracking component 204 comprises one or more optical sensors that are configured to track the movement of the ultrasound probe(s) 202 relative to an initial position (e.g., on the object 208). In another embodiment, the tracking component 204 comprises a magnetic field generator, but the magnetic field generator resides adjacent the object 208 as opposed to underneath it. Thus, the instant disclosure is not meant to be limited in the manner of and/or mechanism(s) for tracking.

The position information (e.g., signals and/or data) yielded from the tracking component 204 and the information (e.g., signals and/or data) indicative of detected echoes yielded from the one or more ultrasound probes 202 is transmitted to a processing unit 206 configured to process the information and display ultrasound images of the object 208 or an aspect thereof being examined on a monitor 210 of the processing unit 206. The processing unit 206 may comprise one or more components for processing the position information and/or the information indicative of detected echoes received from the tracking component 204 and/or the ultrasound probe(s) 202, respectively. For example, the illustrated processing unit 206 comprises a 2D ultrasound imaging component 212, a compiler 214, and a database 216. It will be appreciate that the processing unit 206 may also comprise other components besides those described herein. For example, the processing unit 206 may comprise a keyboard 218 or other input device configured to receive input from a user (e.g., technician) reviewing the images displayed on the monitor 210. For example, the user may adjust the image plane that is being displayed (e.g., to show a different horizontal plane of the object 208 that is closer to the probe 202).

The 2D ultrasound imaging component 212 is configured to process the information received from the ultrasound probe and generate 2D image data indicative of a plane(s) of the object 208 or aspect thereof under examination using image processing. For example, the 2D ultrasound imaging component 212 may be configured to use echo mode processing algorithms, Doppler shift echo processing algorithms, and/or other analytic and/or iterative techniques to convert the information into images. In this way, the information received from ultrasound probe(s) 202 can be converted into a medium that is more understand to a user viewing the data on a monitor 210, for example. Respective images generally represent a plane that is substantially perpendicular to the path ultrasound signals travel. For example, in the illustrated embodiment, the ultrasound probe(s) 202 is configured to emit ultrasound signals downward into the object 208 and resulting images may depict a horizontal plane of the object 208 that goes into and out of the page and/or from left to right on the page.

Moreover, in one embodiment, the 2D ultrasound imaging component 212 may be configured to associate the generated 2D image data with position information (e.g., reference coordinates) indicative of a position of an ultrasound probe 202 relative to the tracking component 204. In this way, it can be determined where, in relation to the tracking component 204 and/or the object, an ultrasound probe 202 was located at the time information and/or data comprised in the generated 2D image data was generated. Thus, respective 2D images may be associated with reference coordinates that are indicative of a location/position of an ultrasound probe 202 at the time the 2D image was generated, for example.

In the example environment 200, the processing unit 206 further comprises a compiler 214 (e.g., a compilation component) configured to use the position information yielded from the tracking component 204 and the 2D image data yielded from the 2D ultrasound imaging component 212 to construct volumetric ultrasound data. Stated differently, analytic, iterative, and/or other techniques for creating volumetric data from one or more ultrasound images (e.g., and/or from the raw information yielded from the ultrasound probe(s) 202) are used to generate a 3D representation of the object 208 or an aspect thereof under examination. For example, based upon the position information, it can be determined how two or more 2D images correlate with one another (e.g., whether two images depict different planes of the same anatomical feature), and based upon identified correlations, volumetric ultrasound data can be generated.

It will be appreciated that as with the CT data generated in the example environment 100 of FIG. 1, the ultrasound volumetric data and/or the 2D image data may be stored in a database 216 (e.g., a computer-readable storage unit such as a hard drive, flash drive, solid state drive, etc.) for later retrieval. Moreover, while reference is made herein to the database 216 being comprised in the processing unit 206, the database 216 and/or other components of the ultrasound modality illustrated in the example environment 200 may be comprised elsewhere and the processing unit 206 may transmit the information to the database 216 (e.g., via a network), for example.

As an example of a typical use for examining an object (e.g., a patient) using a first image modality (e.g., as illustrated in FIG. 1) and an ultrasound modality (e.g., as illustrated in FIG. 2), suppose a patient has a tumor in and/or beside his/her kidney that needs to be biopsied and/or removed. Several days and/or weeks prior to the treatment (e.g., surgery), the patient may undergo an examination using the first image modality (e.g., a CT image modality, ultrasound modality, MRI modality, etc.) to generate volumetric data indicative of the tumor and/or surrounding areas of the tumor to give a surgeon information that may be useful in developing a treatment plan. For example, the surgeon may use the volumetric data and/or images derived therefrom to determine a best approach for performing the biopsy and/or extraction to mitigate harm to nearby organs and/or to mitigate damage to nearby arteries.

Once a treatment plan has been developed using the first image modality and the patient is prepped for the surgery, the surgeon may proceed with performing an ultrasound on the patient to identify the organs and/or arteries the surgeon wishes to avoid. That is, the orientation/position of the patient during the CT examination and the orientation/position of the patient on the operating table may be different (e.g., causing the organs and/or arteries to shift), so the surgeon may perform an examination of the patient prior to the surgery using a second image modality (e.g., an ultrasound modality) to identify/verify the position of the organs and/or arteries. It will be appreciated that in some applications, the first image modality may not be used to reimage the patient at least because of the difficulty of imaging the patient with the first image modality once the patient is prepped for surgery. For example, a CT image modality generally occupies a large amount of space (e.g., and is generally fixed in a particular room). Therefore, prior to surgery, the surgeon may examine (e.g., survey) the patient using a more maneuverable, possibly real-time image modality, such as ultrasound, for example.

Once the organs, arteries, etc. have been identified, the surgeon may proceed with the surgery. It will be appreciated that in some instances, the surgeon may continue using ultrasound during the surgery to monitor the insertion of instruments into the patient. For example, the surgeon may continue to perform an ultrasound of the patient while a surgical tool is being inserted into the patient to monitor the progress of the surgical tool and/or to mitigate the possibility of the surgical tool entering an area the surgeon intends to avoid. Thus, the ultrasound modality may deliver real-time information to the surgeon about the procedure being performed before and/or during a treatment, for example.

To correlate images yielded from the ultrasound modality with images yielded from another image modality, a transformation matrix may be automatically generated that provides information on how to transform a given set of coordinates to derive an image that is acquired from a different image modality. For example, in one embodiment, given a set of coordinates indicative of a position of an ultrasound component relative to an object and/or relative to a tracking component (e.g., 204 in FIG. 2) an image can be derived from the first image modality volumetric data that is representative of a similar perspective of the object as is represented in a displayed ultrasound image.

It will be appreciated that in order to generate the transformation matrix, ultrasound volumetric data may be generated (e.g., by the compiler 214 in FIG. 2) and compared to volumetric data yielded by the first image modality to identify how data from the ultrasound modality relates to data from the first image modality. In this way, it can be determined what image(s), yielded from the first image modality, would correspond to an ultrasound image being displayed based upon the position of an ultrasound component (e.g., 202 in FIG. 2) at the time the image is being displayed, for example. That is, subsequent to the generation of the transformation matrix, it can be determined which image(s) from the first image modality should be displayed based upon real-time position information regarding a position of the ultrasound component relative to the object and/or tracking component, for example.

Figure 3:
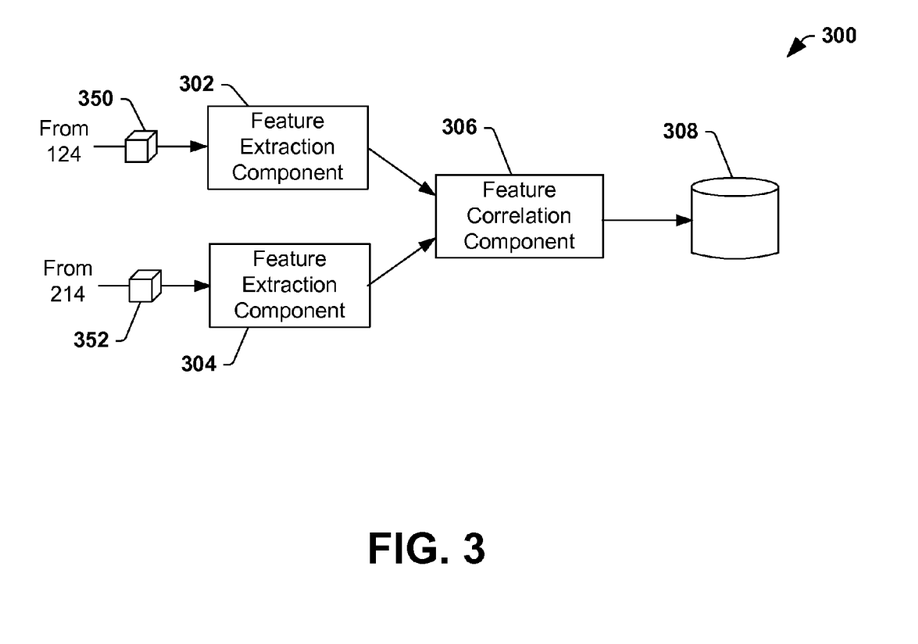
FIG. 3 is an example schematic block diagram of a system for automatically generating a transformation matrix to be used for correlating images.

FIG. 3 illustrates a component block diagram of an example system 300 for automatically correlating volumetric data 350 of an object yielded from a first image modality (e.g., CT, MRI, PET, ultrasound, etc.), and volumetric data 352 of an object yielded from an ultrasound modality. For example, in one embodiment, the automatic correlation comprises generating a transformation matrix (e.g., such as a four-by-four three-dimensional transformation matrix). The transformation matrix is derived using features extracted from the volumetric data set 350 yielded from the first image modality and the volumetric data set 352 of yielded from the ultrasound modality (e.g., or from a compiler 214 in FIG. 2 of an ultrasound modality). Such a transformation matrix may be generated during a calibration phase and/or during a normal examination period. For example, in one embodiment, prior to focusing in on a target to be examined by the ultrasound modality, a technician may perform a brief survey using the ultrasound examination to examine both the target of the examination and surrounding areas. Based upon information collected during this brief survey, an ultrasound volumetric data set 352 may be generated (e.g., by the compiler) and compared with a first image modality volumetric data set 350 to determine a transformation matrix or rather to determine values for a transformation matrix, for example. As will be described in FIG. 4, such a matrix may be used when a subsequent image(s) is produced from an examination of the object using the ultrasound image modality to yield one or more images yielded from the first image modality that correlates with the ultrasound image(s) and/or vice-versa, for example.

Volumetric data 350 yielded from a first image modality (e.g., such as shown in the example environment 100 in FIG. 1) may be referred to herein as, among other things, first image modality volumetric data or a first image modality volumetric data set and volumetric data 352 yielded from an ultrasound modality (e.g., such as shown in the example environment 200 in FIG. 2) may be referred to herein as, among other things, ultrasound volumetric data or an ultrasound volumetric data set. Moreover, the use of the term automatic is not intended to imply that there is a total absence of user input into the process for generating a transformation matrix. For example, a user may verify the transformation matrix as part of the process. Rather, the use of the terms automatic, automatically, and/or the like is intended to merely imply that a majority of the process for generating the transformation matrix is performed in the absence of user input;

although in one embodiment, the generation of the transformation matrix can be performed completely in the absence of user input, for example.

As described above, it will be appreciated that while continued reference is made to a first image modality and an ultrasound modality, the first image modality may, in one embodiment, be an ultrasound modality. For example, a first ultrasound may be performed weeks prior to a surgery to produce a first set of volumetric data and a second ultrasound may be performed the day of the surgery to produce a second set of volumetric data. The first and second sets of volumetric data may then be used by the example system 300 to generate a transformation matrix, for example. Alternatively, the first image modality may not be an ultrasound modality, but may instead be another image modality that is configured to (e.g., capable of) yielding volumetric data, such as CT, PET, MRI, etc. Moreover, while continued reference is made herein to merely two sets of volumetric data, it will be appreciated that the components and/or processes described herein may be used to generate a transformation matrix based upon more than two volumetric data sets. For example, a first volumetric data set may be yielded from a first image modality, a second volumetric data set may be yielded from a second image modality, and a third volumetric data set may be yielded from a third image modality, where the first, second, and third image modalities are different and/or where at least the first and second image modalities are the same image modality.

As will be described in more detail below, generally the values determined for the transformation matrix are based at least in part upon the identification of one or more features (e.g., vessels (e.g., including blood vessels, such as arteries and veins), blood vessel topologies, blood vessel patterns, blood vessels trees, muscle structure, bone structure, etc.) that are identifiable in both the first image modality volumetric data set 350 and the ultrasound volumetric data set 352. Features that are identifiable in both volumetric data sets 350, 352 may be referred to herein as common features. That is, a common feature is used herein to refer to a feature (e.g., anatomical detail such as a same vessel structure, same portion of an organ, etc.) that is identifiable in both the first image modality volumetric data set 350 and the ultrasound volumetric data sets 352 (e.g., and/or in additional other volumetric data sets).

In the illustrated embodiment, a first feature extraction component 302 is configured to receive the first image modality volumetric data set (e.g., from an image reconstructor 124 and/or a database 134 in FIG. 1) and to identify and/or extract features represented in the first image modality volumetric data set 350. Similarly, a second feature extraction component 304 is configured to receive the ultrasound volumetric data set (e.g., from a compiler 214 and/or a database 216 in FIG. 2) and to identify and/or extract features represented in the ultrasound volumetric data set 352. For example, in one embodiment, the first feature extraction component 302 may be configured to scan the first image modality volumetric data set 350 to identify and/or extract features represented therein to generate a first feature set (e.g., indicative of features identified in the first image modality volumetric data set 350), and the second feature extraction component 304 may be configured to scan the ultrasound volumetric data set 352 to identify and/or extract features represented therein to generate a second feature set (e.g., indicative of features identified in the second image modality volumetric data set). It will be appreciated that the features identified in and/or extracted from the first image modality volumetric data set 350 do not have to be the same features as those identified in and/or extracted from the ultrasound volumetric data set 352, although there may be some overlap/common features. That is, at this stage, substantially all identifiable features in one or more of the volumetric data sets 350, 352 may be identified and/or extracted by the respective feature extraction components 302, 304.

It will also be appreciated that while the example system illustrates two feature identification/extraction components 302, 304 respectively configured to scan merely one volumetric data set, in another embodiment, the system may comprise merely one feature identification//extraction component configured to scan multiple volumetric data sets (e.g., from different types of image modalities). Regardless of whether the system comprises one or more feature identification components, the volumetric data sets 350, 352 may or may not be scanned concurrently.

Moreover, in one embodiment, information related to features that are identified and/or extracted from one or more of the volumetric data sets 350, 352 may be stored in one or more databases, for example, and recalled at a later time to be used by the feature correlation component 306. For example, at the time the first image modality volumetric data set 350 was generated (e.g., which may be weeks prior to the acquisition of the ultrasound volumetric data set 352), the first feature extraction component 302 may identify and/or extract features from the first image modality volumetric data set 350 (e.g., and/or this could be performed any time before the acquisition of the ultrasound volumetric data set 352). Information related to such extracted features may then be stored in one or more databases until the ultrasound volumetric data set 352 is generated (e.g., weeks later) and features have been identified and/or extracted from the ultrasound volumetric data set 352 by the second feature extraction component 304. Conversely, information related to features identified and/or extracted from the ultrasound volumetric data set 352 may be stored in one or more databases until features have been identified and/or extracted from the first image modality volumetric data set 350. Thus, information related to features identified and/or extracted from one or more volumetric data sets may be stored in one or more databases and the feature correlation component 306 may retrieve such information at the time of the correlation, for example. Moreover, such information or data (and/or (sub)sets thereof may be repeatedly accessed for subsequent and/or different correlations, for example.

The techniques (e.g., analytic, iterative, and/or other processes) for identifying features may depend upon the image modality from which the volumetric data 350, 352 was acquired. For example, depending at least in part upon the image modality (e.g., and characteristics of the features that can be represented by data yielded from the particular image modality being scanned), features can be identified based at least in part upon density, chemical composition, shape, fluid flow, size, etc.

As an example, respective feature extraction components 302, 304 may be configured to identify blood vessels in respective volumetric data sets 350, 352 and to respectively generate a topology of blood vessel trees based upon the identified blood vessels. In this way, data (e.g., details related to clusters of blood vessels) may be generated from respective volumetric data sets 350, 352 that may be used to correlate the volumetric data sets 350, 352 (e.g., and generate a transformation matrix). In this way, the feature extraction components 302, 304 may generate data that is useful to a feature correlation component 306 to generate a transformation matrix, for example.

The example system 300 also comprises a feature correlation component 306 configured to receive the data generated by the feature extraction components 302, 304 indicative of features that were identified and/or extracted in respective volumetric data sets 350, 352. The feature correlation component 306 is also configured to compare the features identified and/or extracted from the first image modality volumetric data set 350 with the features identified and/or extracted from the ultrasound volumetric data set 352 to determine whether there is a correlation in the volumetric data sets 350, 352. For example, the feature correlation component 306 may compare the identified features yielded from the first image modality volumetric data set 350 with the identified features yielded from the ultrasound volumetric data set 352 to determine whether one more features are common in both volumetric data sets 350, 352.

It will be appreciated that there is a difference between a correlation and a match. That is, a correlation is used herein in a broad sense to mean that there is at least some similarity where a match would generally imply that the two features are nearly identical. For example, a kidney and/or blood vessel pattern represented in the first image modality volumetric data set 350 and a kidney and/or blood vessel pattern represented in the ultrasound volumetric data set 352 may have some correlation, but may not be a perfect match because, for example, the features may be represented as larger, in different orientation, etc. in the first image modality data set 350 than they are in the ultrasound volumetric data set 352. For example, a patient may be in an different orientation during a CT examination than during an ultrasound examination such that a blood vessel pattern is more compressed during one examination than the other, and as may be reflected in respectively resulting images and/or data sets, for example.

Based upon features the are common to both volumetric data sets (e.g., and hence extracted from both data sets) 350, 352 (e.g., or three or more volumetric data sets if the feature correlation component 306 is comparing features extracted from volumetric data sets yielded from three or more image modalities), the feature correlation component 306 may be configured to correlate the features identified and/or extracted from the first image modality volumetric data set 350 with the features identified and/or extracted from the ultrasound volumetric data set 352. In one embodiment, such a correlation may be used to automatically generate a transformation matrix (e.g., such as a four-by-four three-dimensional matrix) configured to specify how a first set of reference coordinates should be transformed to yield a second set of reference coordinates. That is, stated differently, given an image plane yielded from an examination using an ultrasound modality and/or position information indicative of a position of an ultrasound component (e.g., probe) at the time the image plane is generated, the transformation matrix is configured to provide information that causes a substantially similar image plane, yielded from an examination using the first image modality, to be displayed. Thus, the transformation matrix is configured to correlate images from two or more modalities given an image plane of an image yielded from the ultrasound modality and/or vice versa.

In the example embodiment, the generated transformation matrix may be stored in a database 308 and used during future ultrasound imaging of the object (e.g., during a same examination session) to correlate images produce by the ultrasound with images produced from another image modality (e.g., such as CT).

Figure 4:
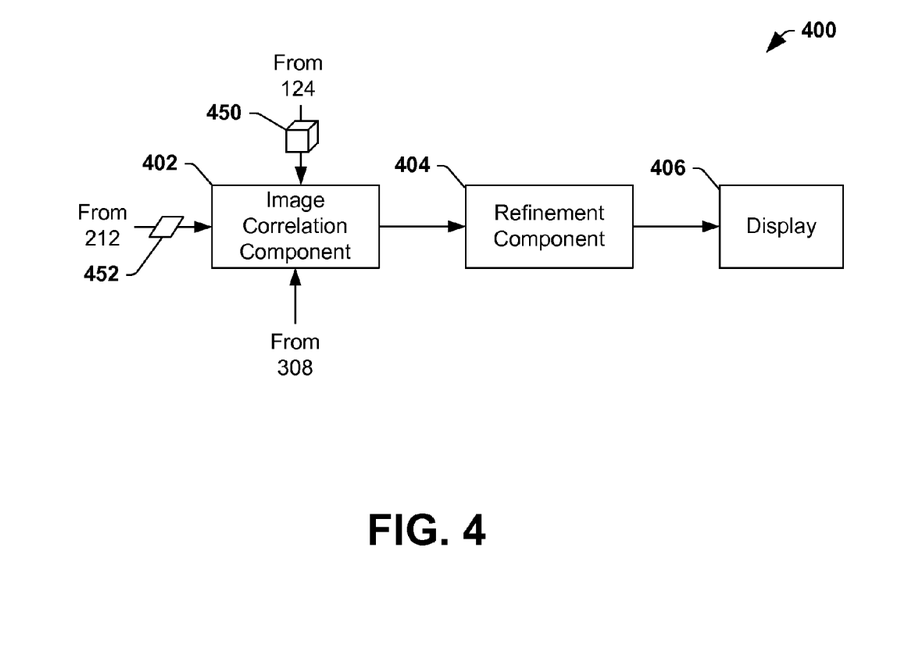
FIG. 4 is an example schematic block diagram of a system for correlating images.

FIG. 4 illustrates a component block diagram of an example system 400 for correlating images using an automatically generated transformation matrix. In this way, an ultrasound image depicting an object from a first perspective may be correlated with an image yielded from a first image modality that depicts the object from a substantially similar perspective and/or vice-versa.

The example system 400 comprises an image correlation component 402, an image refinement component 404, and a display 406. The image correlation component is configured to receive first image modality volumetric data 450 (e.g., 350 in FIG. 3) from an image reconstructor (e.g., 124 in FIG. 1) or database (e.g., 134 in FIG. 1), for example, and to receive one or more ultrasound images 452 (e.g., including position information indicative of a position of an ultrasound component (e.g., probe) relative to a tracking component, for example) from a 2D ultrasound imaging component (e.g., 212 in FIG. 2). It will be appreciated that the one or more ultrasound images 452 may or may not be indicative of data used to generate ultrasound volumetric data (e.g., 352 in FIG. 3) that was used to generate the transformation matrix. For example, in one embodiment, the ultrasound volumetric data may be generated based upon ultrasound signals and/or data received during a first interval of time (e.g., a first 5 minutes of an examination), and the one or more ultrasound images 452 may be generated based upon ultrasound signals and/or data received during a second interval of time (e.g., a 5 second interval following the first 5 minutes of the examination). Thus, the one or more ultrasound images 452 may include data and/or signals included in the ultrasound volumetric data or may not include such data and/or signals.

The image correlation component 402 is further configured to derive an image(s) from the first modality volumetric data set 450 based upon the received one or more ultrasound image 452 (e.g., including the comprised position information) and the automatically generated transformation matrix (e.g., stored in database 308 of FIG. 3). That is, using analytic, iterative, and/or other transformation techniques, it can be determined how to slice the first modality volumetric data set 450 based upon reference coordinates (e.g., position information) included with the one or more ultrasound images 452 to generate an image, yielded from the first image modality, that depicts the object from a perspective that is substantially similar to the perspective of the object in the one or more ultrasound images. In this way, an image acquired using a first image modality may be correlated or fused with an image correlated with a second image modality.

The image correlation component 402 may be further configured to transmit the correlated images to a refinement component 404 that is configured to refine the correlation between the image(s) acquired from the first image modality and the image(s) acquired from the ultrasound modality using analytical and/or iterative techniques. For example, in one embodiment, rigid image registration techniques and/or non-rigid image registration techniques may be applied to one or both of the correlated images. By applying such techniques, the features comprised in one or both of the correlated images may be manipulated (e.g., reoriented, deformed (e.g., stretched, shrunk), magnified, etc.) to cause features comprised in correlated images to appear more similar.

As an example, a similar blood vessel structure may be represented in both an image yielded from the first image modality and a corresponding image (e.g., correlated image) yielded from the ultrasound modality. However, when the patient was examined by the first image modality, the patient may have been in a different position (e.g., sitting down) than the patient was in during the examination by the ultrasound (e.g., at which time the patient may have been lying down). Therefore, despite the correlation by the image correlation component 402, the blood vessel structure may appear slightly more contracted, for example, in the image yielded from the first image modality than in the corresponding image yielded from the ultrasound modality. To improve upon the correlation, the refinement component 404 may use rigid, non-rigid, and/or other image registration techniques, depending upon the characteristics of the differences in the correlated images (e.g., whether the differences are non-linear geometric differences, linear geometric differences, etc.), to stretch the image yielded from the first image modality and/or to shrink the corresponding image yielded from the ultrasound modality, for example, such that the features more closely resemble one another.

In one embodiment, upon the completion of the correlation, refinement, etc. the refinement component 404 may be configured to transmit the refined, correlated images to a display 406 so that at least a portion thereof can be displayed to a user.

It will be appreciated that due to the correlation by the image correlation component 402, images yielded from the first image modality may be combined with images yielded from the ultrasound modality (e.g., such that images yielded from one image modality may overlay images yielded from a second image modality (e.g., to provide a composite multimodality image)). Alternatively, images yielded from the first image modality may be viewed side-by-side with images yielded from the ultrasound modality on the same display 406 and/or on different displays.

Moreover, it will be appreciated that while reference is made herein to the image correlation component 402 deriving an image yielded from the first image modality based at least in part upon the received ultrasound image (e.g., comprising position information), the converse may also true. Stated differently, in another embodiment, the image correlation component 402 may be configured to derive an image yielded from the ultrasound modality based at least in part upon a specified image yielded from the first image modality. For example, in such an embodiment, the image correlation component 402 may receive an image yielded from the first image modality and receive ultrasound volumetric data (e.g., 352 in FIG. 3) from a compiler (e.g., 214 in FIG. 2). Based upon the received image and the transformation matrix, the image correlation component 402 may be configured to derive an ultrasound image that correlates with the received image yielded from the first image modality, for example. Similarly, both an ultrasound image and an image from another modality may be adjusted (based on/relative to one another).

Figure 5:
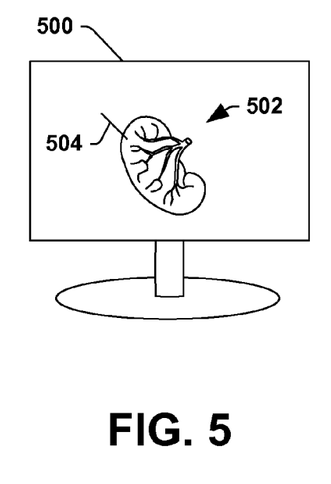
FIG. 5 illustrates an example image yielded from an ultrasound examination.
Figure 6:
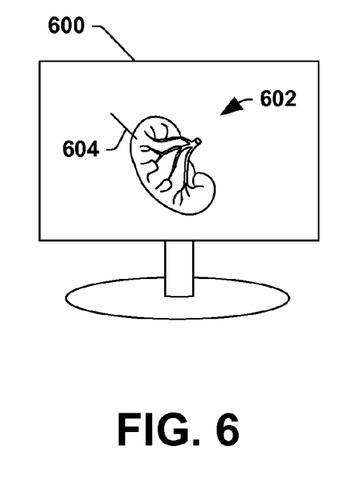
FIG. 6 illustrates an example image yielded from a first image modality volumetric data set.
Figure 7:
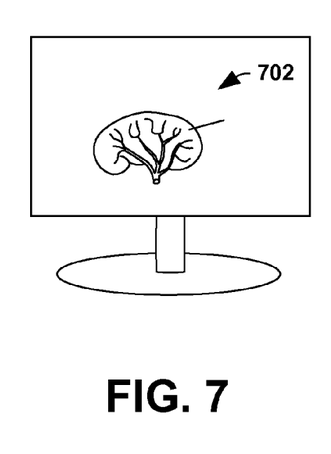
FIG. 7 illustrates an example image yielded from an ultrasound examination.
Figure 8:
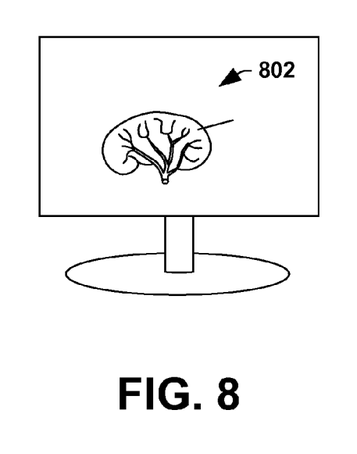
FIG. 8 illustrates an example image yielded from a first image modality volumetric data set.

FIGS. 5-8 illustrate example displays 500, 600, 700, 800 respectively comprising images 502, 602, 702, 802 that may be displayed to a user during a procedure, for example. More particularly, FIG. 5 illustrates an ultrasound image 502 (e.g., 452 in FIG. 4) depicting an object from a first perspective, and FIG. 6 illustrates a derived image 602 yielded from a first image modality volumetric data set (e.g., 450 in FIG. 4). The derived image 602 may be derived by an image correlation component (e.g., 402 in FIG. 4) based upon, among other things, the first image modality volumetric data set, the ultrasound image 502, and an automatically generated transformation matrix, for example. It will be appreciated that the derived image 602 depicts the object from substantially the same perspective as the ultrasound image 502 in FIG. 5. Thus, FIGS. 5 and 6 may be said to illustrate fused images (e.g., depicting a substantially similar scene from two different image modalities). Moreover, FIG. 7 illustrates a second ultrasound image 702 depicting the object from a second perspective, and FIG. 8 illustrates a second derived image 802 yielded from the first image modality volumetric data set. The second derived image 802 may be derived based upon, among other things, the first image modality volumetric data set, the second ultrasound image 702, and the automatically generated transformation matrix. It will be appreciated that the second ultrasound image 702 and the second derived image 802 depict the object from a substantially same perspective (e.g., such that the second ultrasound image 702 and the second derived image 802 are fused images illustrating a substantially same scene from two different image modalities). Because of the correlation between the substantially similar images 502, 602 and 702, 802 (e.g., respective sets of images represent substantially the same anatomical features from substantially the same viewpoint), a surgeon may be able to view adjacent displays (e.g., or a split screen of the same display), depicting substantially similar viewpoints of the object from two or more image modalities with little to no user input (e.g., besides selecting a particular viewpoint to view the object from in at least one of the two or more image modalities).

As described above, it will be appreciated that one or more of the images (e.g., such as the ultrasound images) can be acquired in real-time and correlated with one or more images derived from a volumetric data set that was previously acquired using the automatically generated transformation matrix. For example, in one embodiment, the first image modality volumetric data set from which the derived image 602 is derived can be acquired during an examination that occurred weeks prior to a surgery, and the ultrasound image can be acquired in real-time during a surgery, for example. Based upon position information associated with the ultrasound image 502 (e.g., indicative of a position of an ultrasound component (e.g., 202 in FIG. 2) at the time the ultrasound image 502 is generated) and the automatically generated transformation matrix, the derived image 602 can be derived from the first image modality volumetric data set such that the ultrasound image 502 and the derived image 602 yielded from the first image modality can be displayed concurrently (e.g., even though the first image modality volumetric data set may have been acquired weeks before the presently occurring ultrasound examination).

It will be appreciated that by generating images in real-time during a surgery, a surgeon can image a patient as a surgical instrument is being inserted into the patient. For example, a surgeon may insert a surgical instrument into the kidney while an ultrasound of the kidney is being performed and a representation of the surgical instrument 504 may be displayed within the ultrasound image 502 that is being acquired in real-time. Moreover, due to the automatically generated transformation matrix, a representation of the surgical instrument 604 may be displayed within the derived image 602 derived from the first image modality volumetric data. That is, even though the first image modality volumetric data may have been acquired during an examination that took place prior to the surgical instrument being inserted into the patient, a representation of the surgical instrument 604 may be imposed upon the derived image 602 as though the first image modality volumetric data was being acquired in real-time as the surgery is taking place. Thus, based upon the representation of the surgical instrument 504 in the ultrasound image 502, a similar representation of the surgical instrument 604 may be automatically imposed on the derived image 602 illustrated in FIG. 6.

Moreover, a change in an image(s) yielded from an ultrasound modality may cause a similar change in an image(s) derived from the first image modality volumetric data set. For example, suppose that a surgeon reorients the ultrasound component, causing a second ultrasound image 702, depicting the object from a different perspective than what is illustrated in the ultrasound image 502, to be generated. Such a change may further cause the derived image to change from the image 602 illustrated in FIG. 6 to the image 802 illustrated in FIG. 8. Thus, by manipulating images yielded from a first image modality, images yielded from another image modality may be automatically manipulated in a corresponding manner.

Figure 9:
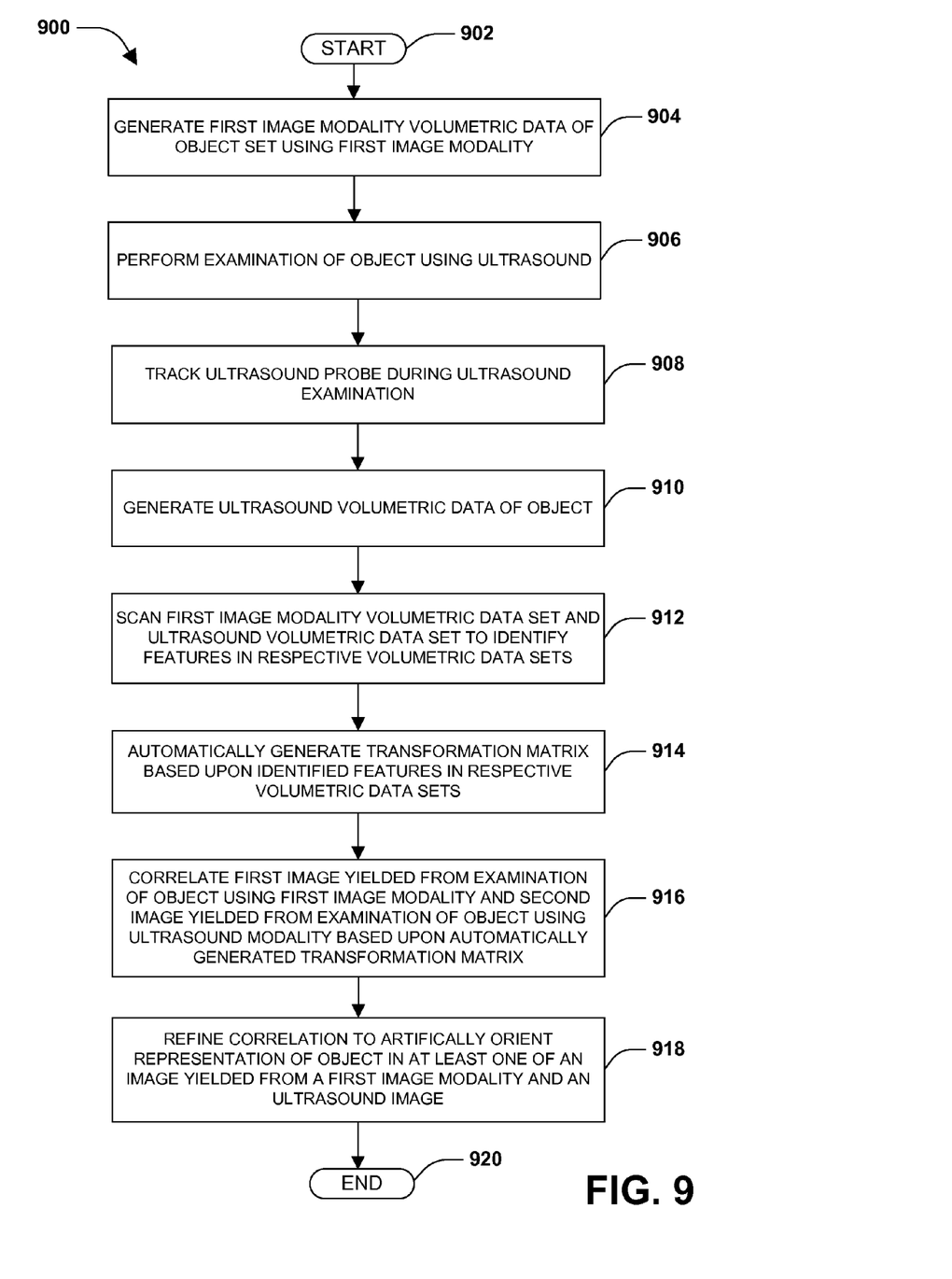
FIG. 9 is an example flow diagram illustrating an example method of automatically correlating volumetric data yielded from two image modalities.

FIG. 9 illustrates an example method 900 for multi-modality image registration. More particularly, FIG. 9 illustrates an example method 900 for correlating images yielded from one or more image modalities (e.g., but preferably two or more different image modalities) based upon an automatically generated transformation matrix (e.g., a four-by-four three-dimensional matrix). Such a method may be useful for correlating images yielded from a CT scan, PET scan, MRI scan, etc. with images yielded from an ultrasound and/or for correlating images yielded from an ultrasound taken during a first interval of time with images yielded from an ultrasound taken during a second interval of time (e.g., days, weeks, or months later).

The example method 900 begins at 902 and first image modality volumetric data of an object is generated using a first image modality at 904. For example, a CT scan, MRI scan, PET scan, etc. of an object may be performed and volumetric data may be generated. It will be appreciated that the techniques used to generate the volumetric data (e.g., in image space) is generally dependent upon the type of scan performed. Therefore, at least for purposes of brevity, such techniques are not described in detail herein.

The example method 900 also includes performing an examination of the object using ultrasound at 906. It will be appreciated that while the example method 900 describes the act of generating first image modality volumetric data before the act of performing an examination of the object using ultrasound, either act may be performed first and/or the acts may be performed substantially concurrently. Moreover, it will appreciated that the object may be in a same and/or different orientation and/or position during the examination using ultrasound as it was during the examination by the first image modality. Thus, for example, the first image modality may examine a patient while the patient is standing upright and/or sitting down and the ultrasound may examine the patient while the patient is lying on his/her back.

Generally, during an examination of an object using ultrasound, ultrasound signals (e.g., sound waves generally in the frequency range of 2 MHz to 10 MHz) are emitted from one or more ultrasound probes toward the object under examination and echoes (e.g., reflected ultrasound waves) are detected by the same and/or different ultrasound probes. Based upon the received echoes, one or more 2D images respectively representing a plane of the object (e.g., absent a dimension the ultrasound waves were emitted into) are produced using analytical, iterative, or other techniques (e.g., echo mode processing algorithms, Doppler shift echo processing algorithms, etc.).

At 908 in the example method 900, the one or more ultrasound probes are tracked during the ultrasound examination to generate position information. For example, magnetic sensors (e.g., such as a magnetic mat) and/or optical sensors may be placed nearby and/or within the ultrasound probe(s) to map the movement of the ultrasound probe(s) relative to the sensors and/or relative to the patient. In this way, it can be determined which 2D images represent a substantially similar portion of the object. For example, it can be determined whether two images representing parallel planes of the object at least partially represent a same aspect (e.g., organ) of the object at different focal spots (e.g., such that the two images could be stacked on top of one another to form a partial 3D view of the aspect of the object).

At 910 in the example method 900, ultrasound volumetric data of the object is generated. For example, in one embodiment, using the 2D ultrasound images (e.g., two-dimensional data sets) and position information acquired from tracking the ultrasound probe(s), a substantially volumetric representation of the object can be generated. That is, because information about the position of one or more ultrasound probes during the acquisition of information represented in respective images is known, the ultrasound information can be constructed into a volumetric representation of the object using analytic, iterative, or other techniques.

At 912 the first image modality volumetric data and the ultrasound volumetric data are scanned to identify and/or extract features in respective volumetric data sets. It will be that techniques for scanning respective volumetric data sets may depend upon the image modality from which the respective volumetric data set was acquired. For example, techniques for scanning CT volumetric data sets to identify and/or extract features represented therein may not be successful for scanning ultrasound volumetric data sets or vice-versa. Moreover, the types of features that are identified and/or extracted may depend upon the image modality used to produce the volumetric data being scanned. However, anatomical features that are generally identifiable in image modalities (e.g., if the object is a human or animal) include, but are not limited to bones, organ tissue, tumor cells, and/or vessels (e.g., such as blood vessels including arteries and/or veins). In other objects (e.g., non-human and non-animal objects), regions of higher or lower density, for example, may be identifiable as features in the volumetric data sets. In one embodiment, where blood vessels are identified, a topology of the blood vessels in respective volumetric data sets may be determined (e.g., mapped) and used in correlating a first image modality volumetric data set and an ultrasound volumetric data set to generate a transformation matrix (e.g., as described below), for example.

As described with respect to FIG. 3, during the feature identification at act 912, it is typically not required that identical features are found in respective volumetric data sets. That is, while it is preferential that at least some of the same and/or similar features be found in respective volumetric data sets (e.g., so that there is something to reference during a later correlation/generation of the transformation matrix), features may be identified in the first image modality volumetric data set that are not identifiable in the ultrasound volumetric data set and/or vice-versa. That is, in at least one embodiment, the goal of the scans is to identify any and/or all of the features that are identifiable in respective volumetric data sets. Although, in another embodiment the goal may be to merely identify features that are identifiable in both volumetric data set(s) (e.g., or in all the volumetric data sets where more than two volumetric data sets are scanned). For example, if it is generally difficult to identify a particular type of tissue in volumetric data yielded from an ultrasound examination, the feature may be excluded from identification in volumetric data yielded from another image modality because the identification of such a feature in the volumetric data yielded from the another image modality would not be useful to generating a transformation matrix (e.g., because it is unlikely that such a feature would be identified in volumetric data yielded from an ultrasound).

At 914 in the example method 900, the features identified/extracted from the ultrasound volumetric data set are correlated with features identified/extracted from the first image modality volumetric data set to automatically generate a transformation matrix That is, one or more features that were identified in the ultrasound volumetric data set at 912 and one or more features that were identified in the first image modality volumetric data set at 912 are compared to determine whether a same and/or substantially similar feature was identified if both volumetric data sets. Based upon commonalities in the compared features, a transformation matrix may be automatically generated.

For example, vessels (e.g., blood vessels such as arteries and veins) are generally identifiable in both ultrasound images and in CT images. Therefore, during the automatic generation at 914, it may be determined whether a pattern of vessels represented in the ultrasound volumetric data substantially matches a pattern of vessels represented in the CT volumetric data. If the patterns substantially match, such a pattern may be used for generating a transformation matrix.

The transformation matrix may comprise a matrix for image fusion. For example, in one embodiment, the transformation matrix is a four-by-four three-dimensional transformation matrix. Generally, such a matrix is configured to specify how to derive an image from a volumetric data set based upon reference points comprised in another image. For example, the transformation matrix may specify how to derive a CT image from a CT volumetric data set based upon reference points in an ultrasound image (e.g., or based upon position information comprised with the ultrasound image data indicative of a position of an ultrasound component (e.g., probe) at the time the ultrasound image is generated).

At 916, an image yielded from the examination of the object using the first image modality is correlated with an image yielded from the examination of the object using the ultrasound modality based at least in part upon the automatically generated transformation matrix. Stated differently, an image yielded from the first image modality may be derived from the first image modality volumetric data set based at least in part upon the ultrasound image (e.g., comprising position information) and the transformation matrix using transformation techniques. Alternatively, an ultrasound image may be derived from the ultrasound volumetric data set based at least in part upon an image yielded from the first image modality and the transformation matrix using transformation techniques. In this way one or more ultrasound images may be registered with one or more images yielded from the first image modality, for example (e.g., such that as a user alters the perspective of the object in images yielded from one image modality from a first perspective to a second perspective, images yielded from another image modality are automatically altered to depict the object from the second perspective as opposed to the first perspective).

In one embodiment, the example method 900 may further comprise refining the correlation at 918 to artificially orient a representation of the object in at least one of an image yielded from the first image modality and an ultrasound image using refinement techniques (e.g., rigid fusion techniques, non-rigid fusion techniques, etc.). The terms artificially orient are used herein to refer to a manipulation of image data that goes beyond a mere correlation. For example, at least one or more portions of at least one of the images may be stretched, turned, collapsed, smoothed etc. to improve the correlation (e.g., or match) between the two or more images (e.g., yielded from different image modalities). In this way, the images yielded from the first image may better match images yielded from the ultrasound modality, for example.

The example method 900 ends at 920.

Figure 10:
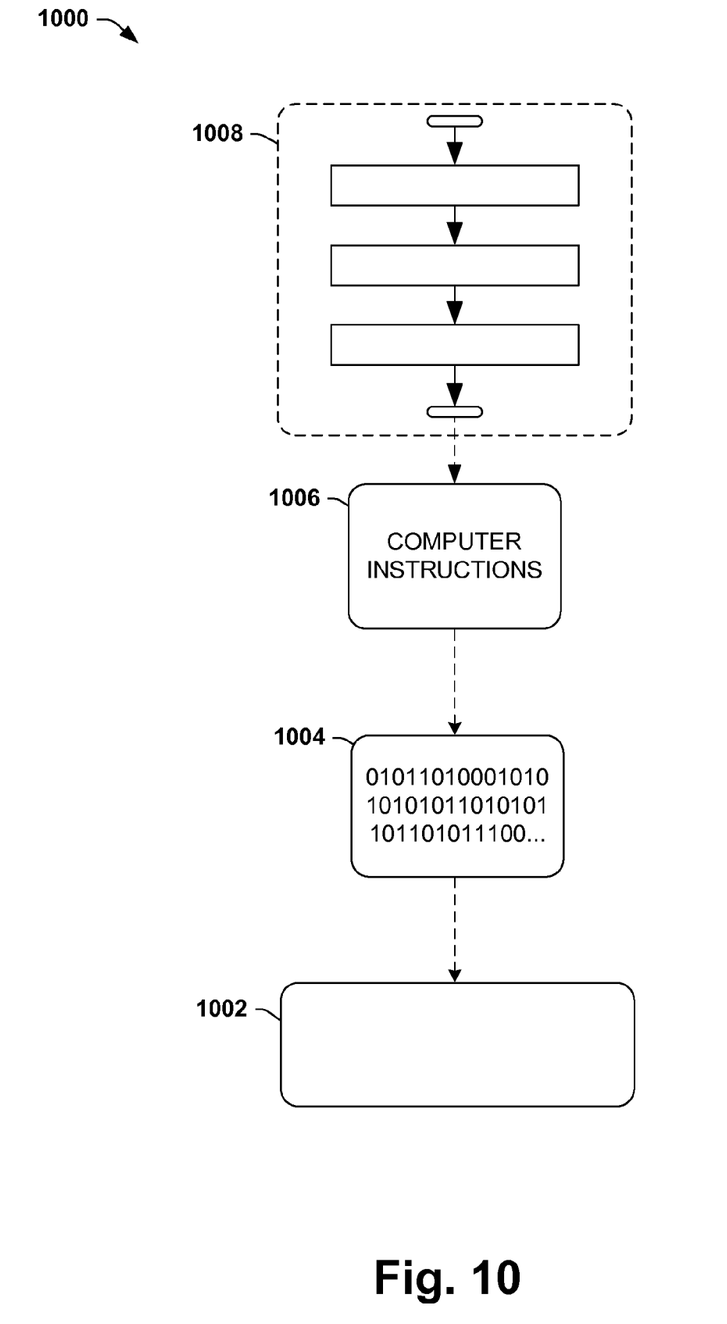
FIG. 10 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein. An example computer-readable medium that may be devised in these ways is illustrated in FIG. 10, wherein the implementation 1000 comprises a computer-readable medium 1002 (e.g., a flash drive, CD-R, DVD-R, or a platter of a hard disk drive), on which is encoded computer-readable data 1004. This computer-readable data 1004 in turn comprises a set of computer instructions 1006 configured to operate according to one or more of the principles set forth herein. In one such embodiment 1000, the processor-executable instructions 1006 may be configured to perform a method 1008, such as at least some of the example method 900 of FIG. 9, for example. In another such embodiment, the processor-executable instructions 1006 may be configured to implement a system, such as at least some of the exemplary system 300 of FIG. 3, for example. Many such computer-readable media may be devised by those of ordinary skill in the art that are configured to operate in accordance with one or more of the techniques presented herein.

Moreover, the words "example" and/or "exemplary" are used herein to mean serving as an example, instance, or illustration. Any aspect, design, etc. described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form. Also, at least one of A and B or the like generally means A or B or both A and B.

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. A multi-modality image correlation method, comprising:
   during a surgical operation in which an instrument is inserted into a patient at a first location:
     imaging the patient via an ultrasound probe to generate ultrasound information; and
     tracking movement of the ultrasound probe relative to the patient to generate tracking information;
   generating a volumetric ultrasound image using the ultrasound information and the tracking information, the volumetric ultrasound image comprising a representation of the instrument within the patient at the first location;
   spatially correlating, based at least in part upon a transformation matrix, a volumetric image with the volumetric ultrasound image, wherein the volumetric image is yielded from an examination of the patient using a first image modality other than the ultrasound probe and wherein the instrument is not inserted into the patient at the first location during the examination of the patient using the first image modality and wherein the volumetric image does not comprise a representation of the instrument; and
   imposing the instrument on the volumetric image responsive to the correlating such that the instrument appears to be present within the patient at the first location during the examination of the patient using the first image modality.

2. The method of claim 1, comprising generating the transformation matrix, comprising:
   identifying a feature in the volumetric image;
   identifying the feature in the volumetric ultrasound image; and
   comparing a spatial position of the feature in the volumetric image with a spatial position of the feature in the volumetric ultrasound image to generate the transformation matrix.

3. The method of claim 1, the generating comprising:
   generating the volumetric ultrasound image from two or more two-dimensional data sets acquired during the imaging.

4. The method of claim 1, the first image modality comprising a computed tomography image modality.

5. The method of claim 1, the first image modality comprising a magnetic resonance image modality.

6. The method of claim 1, comprising generating the transformation matrix based at least in part upon a feature in the volumetric image and a feature in the volumetric ultrasound image.

7. The method of claim 6, the feature in the volumetric image and the feature in the volumetric ultrasound image representing a same anatomical feature of the patient.

8. The method of claim 7, the same anatomical feature comprising at least one of a blood vessel, a blood vessel pattern, or a topology of blood vessels trees.

9. A system for multi-modality image correlation, comprising:
   a tracking component configured to track movement of an ultrasound probe relative to a patient during a surgical operation in which an instrument is inserted into the patient at a first location to generate tracking information;
   a volumetric data generator configured to generate a volumetric ultrasound image using ultrasound information generated by the ultrasound probe during the surgical operation and the tracking information, the volumetric ultrasound image comprising a representation of the instrument within the patient at the first location; and
   an image correlation component configured to:
     spatially correlate, based at least in part upon a transformation matrix, a volumetric image with the volumetric ultrasound image, wherein the volumetric image is yielded from an examination of the patient using a first image modality other than the ultrasound probe and wherein the instrument is not inserted into the patient at the first location during the examination of the patient using the first image modality and wherein the volumetric image does not comprise a representation of the instrument, and
     impose the instrument on the volumetric image responsive to spatially correlating the volumetric image with the volumetric ultrasound image such that the instrument appears to be present within the patient at the first location during the examination of the patient using the first image modality.

10. The system of claim 9, comprising a feature extraction component configured to:
    identify a feature in the volumetric image; and
    identify the feature in the volumetric ultrasound image.

11. The system of claim 10, comprising a feature correlation component configured to generate the transformation matrix based at least in part upon identifying the feature in the volumetric image and identifying the feature in the volumetric ultrasound image.

12. The system of claim 10, the feature comprising a representation of at least one of a blood vessel, a blood vessel pattern, or a topology of blood vessels trees.

13. The system of claim 9, the volumetric data generator configured to
    compile two or more two-dimensional ultrasound images generated by the ultrasound probe based at least in part upon the tracking information to generate the volumetric ultrasound image.

14. The system of claim 9, the tracking component implementing at least one of an active tracking technique or a passive tracking technique.

15. The system of claim 9, the first image modality comprising a computed tomography image modality.

16. The system of claim 9, comprising a feature correlation component configured to generate the transformation matrix in the absence of user input.

17. The system of claim 9, comprising a refinement component configured to refine a correlation of the volumetric image and the volumetric ultrasound image using at least one of a rigid fusion technique or a non-rigid fusion technique.

18. A non-transitory computer-readable storage medium comprising computer executable instructions that when executed perform a method, comprising:
    during a surgical operation in which an instrument is inserted into a patient at a first location:
      imaging the patient via an ultrasound probe to generate ultrasound information; and
      tracking movement of the ultrasound probe relative to the patient to generate tracking information;
    generating a volumetric ultrasound image using the ultrasound information and the tracking information, the volumetric ultrasound image comprising a representation of the instrument within the patient at the first location;
    spatially correlating, based at least in part upon a transformation matrix, a volumetric image with the volumetric ultrasound image, wherein the volumetric image is yielded from an examination of the patient using a first image modality other than the ultrasound probe and wherein the instrument is not inserted into the patient at the first location during the examination of the patient using the first image modality and wherein the volumetric image does not comprise a representation of the instrument; and imposing the instrument on the volumetric image responsive to the correlating such that the instrument appears to be present within the patient at the first location during the examination of the patient using the first image modality.

19. The non-transitory computer-readable storage medium of claim 18, the method comprising:

comparing a set of identifiable features in the volumetric image with a set of identifiable features in the volumetric ultrasound image to identify a feature that is identifiable in both the volumetric image and volumetric ultrasound image; and generating the transformation matrix based at least in part upon the feature that is identifiable in both the volumetric image and the volumetric ultrasound image.

20. The non-transitory computer-readable storage medium of claim 18, the first image modality comprising a computed tomography image modality.

* * * * *